(12) United States Patent
Sinisi et al.

(10) Patent No.: US 12,011,152 B2
(45) Date of Patent: Jun. 18, 2024

(54) TRICUSPID RETRACTOR BLADE ASSEMBLY

(71) Applicant: USB Medical Limited, Hatboro, PA (US)

(72) Inventors: John J Sinisi, Warminster, PA (US); Jesse Sinisi, Warminster, PA (US); Stephen T Epstein, Newtown, PA (US); Mario Castillo-Sang, Cincinnati, OH (US); Rochus K Voeller, Eagan, MN (US)

(73) Assignee: USB Medical Limited, Hatboro, PA (US)

( * ) Notice: Subject to any disclaimer, the term of this patent is extended or adjusted under 35 U.S.C. 154(b) by 206 days.

(21) Appl. No.: 17/529,240

(22) Filed: Nov. 17, 2021

(65) Prior Publication Data

US 2023/0149006 A1    May 18, 2023

(51) Int. Cl.
*A61B 17/02* (2006.01)
*A61B 17/00* (2006.01)
*A61B 17/12* (2006.01)

(52) U.S. Cl.
CPC .... *A61B 17/0218* (2013.01); *A61B 17/00234* (2013.01); *A61B 2017/00243* (2013.01); *A61B 2017/0237* (2013.01); *A61B 17/12013* (2013.01)

(58) Field of Classification Search
CPC .......... A61B 17/0218; A61B 17/00234; A61B 17/12013; A61B 2017/00243; A61B 2017/0237; A61B 17/0206
USPC .................................................. 600/201–245
See application file for complete search history.

(56) References Cited

U.S. PATENT DOCUMENTS

| | | | |
|---|---|---|---|
| 4,151,837 A * | 5/1979 | Millard, Jr. | A61B 1/24 600/226 |
| 5,613,937 A | 3/1997 | Garrison et al. | |
| 6,074,343 A | 6/2000 | Nathanson et al. | |
| 6,254,533 B1 * | 7/2001 | Fadem | A61B 17/0293 600/233 |
| 6,283,912 B1 | 9/2001 | Hu et al. | |
| 6,893,394 B2 | 5/2005 | Douglas et al. | |
| 8,162,962 B2 | 4/2012 | Poo et al. | |
| 8,388,525 B2 | 3/2013 | Poo et al. | |

(Continued)

FOREIGN PATENT DOCUMENTS

| | | |
|---|---|---|
| CA | 2286929 | 4/2001 |
| CN | 103462656 | 1/2016 |

(Continued)

*Primary Examiner* — Eduardo C Robert
*Assistant Examiner* — Tara Rose E Carter
(74) *Attorney, Agent, or Firm* — LaMorte & Associates P.C.

(57) ABSTRACT

A retractor with a specialized blade head assembly. The blade head assembly has a central plate. The central plate extends between a first side edge and a second side edge. A first rotatable arm is attached to the first side edge with a first hinge joint. A second rotatable arm is attached to the second side edge with a second hinge joint. Both rotatable arms can be rotated about the hinge joints. Both the first hinge joint and the second hinge joint are friction hinges that require a threshold force to move. An elongated shaft interconnects with the central plate at a pivot joint. The elongated shaft can be attached to the blade head assembly after the blade head assembly has been inserted into a patient's body.

19 Claims, 5 Drawing Sheets

(56) References Cited

U.S. PATENT DOCUMENTS

| | | | |
|---|---|---|---|
| 8,409,087 B2 | 4/2013 | Ames et al. | |
| 8,460,185 B2 | 6/2013 | Epstein et al. | |
| 9,402,614 B2 | 8/2016 | Fehling et al. | |
| 9,949,814 B2 | 4/2018 | Alexader et al. | |
| D846,119 S | 4/2019 | Greeley et al. | |
| D858,761 S | 9/2019 | Sterry | |
| 10,617,524 B2 | 4/2020 | Van Bladel et al. | |
| 10,736,618 B2 | 8/2020 | Greeley et al. | |
| 10,792,028 B2 | 10/2020 | Beck et al. | |
| 11,039,824 B1 | 6/2021 | Sterry | |
| 2002/0068855 A1 | 6/2002 | Daniel et al. | |
| 2004/0143163 A1 | 7/2004 | Palmer et al. | |
| 2004/0225196 A1 * | 11/2004 | Ruane | A61B 17/0206 600/220 |
| 2010/0286485 A1 | 11/2010 | Valentini et al. | |
| 2011/0046448 A1 | 2/2011 | Paolitto et al. | |
| 2011/0137128 A1 * | 6/2011 | Poo | A61B 17/0293 600/206 |
| 2015/0173733 A1 | 6/2015 | Ryshkus et al. | |
| 2015/0282795 A1 * | 10/2015 | Schabert | A61B 17/0218 600/213 |
| 2020/0305856 A1 | 10/2020 | Bernstein | |

FOREIGN PATENT DOCUMENTS

| | | | | |
|---|---|---|---|---|
| CN | 109464170 | 9/2020 | | |
| DE | 102012219727 | 4/2014 | | |
| ES | 2557517 | 11/2016 | | |
| WO | WO-2004062489 A1 * | 7/2004 | | A61B 1/32 |
| WO | WO 2007/075903 A2 | 7/2007 | | |
| WO | WO-2007075903 A2 * | 7/2007 | | A61B 17/0218 |
| WO | WO 2019/152500 | 8/2019 | | |

\* cited by examiner

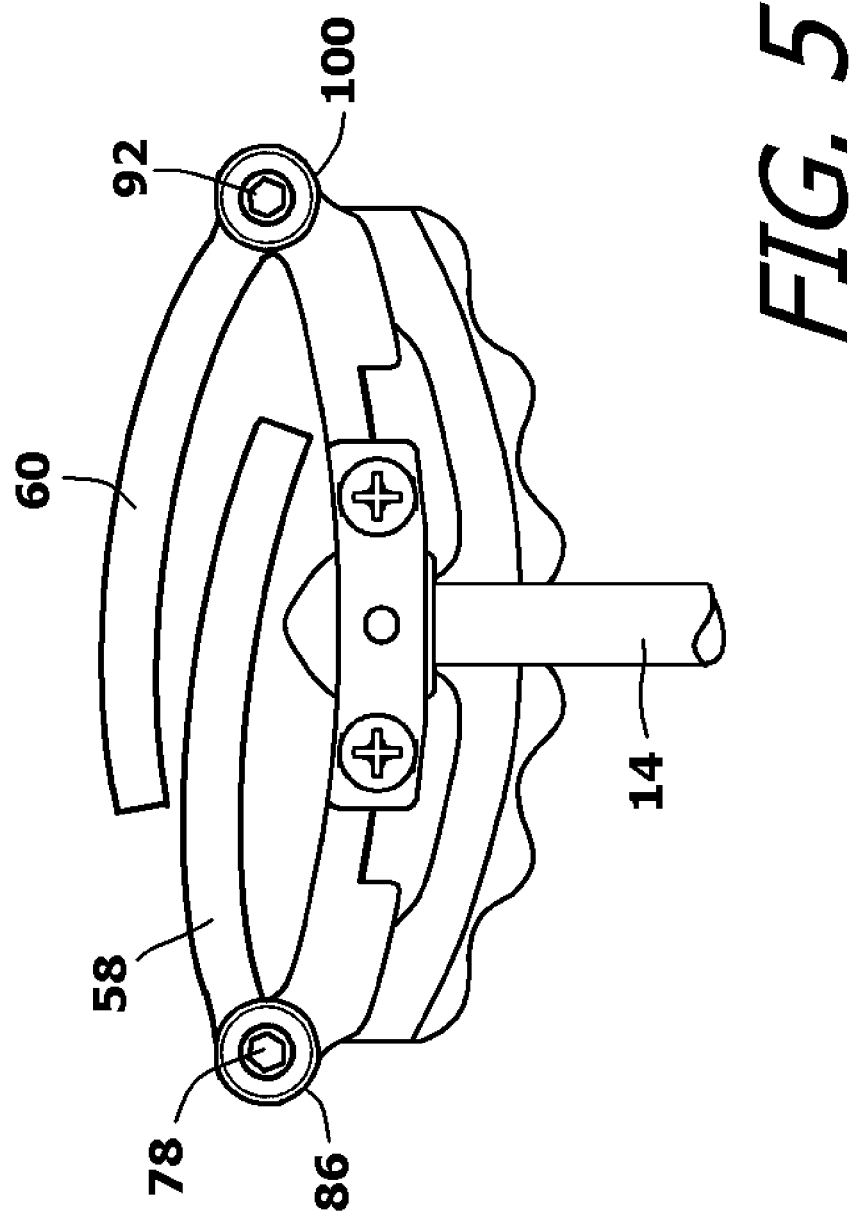

TRICUSPID RETRACTOR BLADE ASSEMBLY

BACKGROUND OF THE INVENTION

1. Field of the Invention

In general, the present invention relates to blade retractors that are used during surgical procedures. More particularly, the present invention relates to surgical retractors having blades that can be selectively adjusted in orientation to meet the needs of a surgeon.

2. Prior Art Description

Surgical retractors are used to manipulate tissue during surgery. Simple retractors have a blade head at the end of an elongated handle that is typically used to push or pull tissue away from a targeted area. More complex retractors have blade heads that can be manipulated to either separate or compress tissue as the retractor is manipulated. Retractors can be made for general use or can be specifically designed for particular surgical procedures. For example, the Cosgrove™ mitral valve retractor sold by Kapp Surgical Instrument Inc., and the cardiac tissue retractor disclosed in U.S. Patent Application Publication No. 2011/0046448 to Paolitto are both retractors that are specifically designed to move cardiac tissue during valve replacement surgery.

A problem associated with many prior art retractors is that they have blade heads that are cumbersome. As such, many prior art retractors are limited to use during invasive surgical procedures. However, in modern surgery, invasive surgical procedures are becoming less common. Rather, many traditionally invasive surgical procedures are being replaced with minimally invasive surgical procedures. In a minimally invasive surgical procedure, very small incisions are made into the body. Elongated instruments are then inserted into the small incisions to access the area within the body cavity needing surgery. The small incisions cause much less injury to the body than does an invasive surgical procedure. Accordingly, the patient typically recovers more rapidly from the surgery with less adverse side effects.

During some surgical procedures, such as heart valve surgery, a specialized retractor is needed to manipulate the heart muscle so that unobstructed access is provided to the surgical site. However, if the surgery is minimally invasive, traditional retractors cannot be brought into the surgery site. The surgeon is therefore limited to small retractors and probes that can be inserted through the small surgical incisions. These retractors are typically inadequate in their capabilities. Furthermore, the space available to manipulate the retractors is severely limited by the surgical incisions. As a result, a small retractor cannot always be manipulated into a position where it is of the most use to the surgeon.

In U.S. Pat. No. 8,460,185 to Epstein, a retractor system is disclosed that is intended for use during a minimally intrusive surgical procedure. However, the size of the blade head utilized on the retractor is directly proportional to the size of the incision that must be made in the body. This is because the blade head must be passed through the incision when entering the body. Accordingly, a surgeon must balance the size of the retractor against the size of the incision.

A need therefore exists for a specialized retractor having an expandable blade head that can be used in a minimally invasive surgical procedure. In this manner, the blade head can be inserted into the body through a small incision and then expanded into a larger size within the body. A need also exists for a retractor system, where a blade can be selectively configured into different shapes in order to better serve the needs of the surgeon. In this manner, one retractor system can be utilized in a large array of roles during a surgical procedure. These needs are met by the present invention as described and claimed below.

SUMMARY OF THE INVENTION

The present invention is a retractor with a specialized blade head assembly. The blade head assembly has a central plate. The central plate extends between a first side edge and a second side edge. A first rotatable arm is attached to the first side edge of the central plate with a first hinge joint. The first rotatable arm can be rotated about the first hinge joint through a first range of motion. A second rotatable arm is attached to the second side edge of the central plate with a second hinge joint. The second rotatable arm can be rotated about the second hinge joint through a second range of motion. Both the first hinge joint and the second hinge joint are friction hinges that require a threshold force to move. The threshold force is selectively adjustable.

An elongated shaft interconnects with the central plate at a pivot joint midway between the first side edge and the second side edge. The elongated shaft can be attached to the blade head assembly after the blade head assembly has been inserted into a patient's body.

BRIEF DESCRIPTION OF THE DRAWINGS

For a better understanding of the present invention, reference is made to the following description of an exemplary embodiment thereof, considered in conjunction with the accompanying drawings, in which:

FIG. 5 is a bottom view of the blade head assembly shown in a closed configuration.

DETAILED DESCRIPTION OF THE DRAWINGS

Although the present invention retractor can be embodied in different ways for different surgical procedures, the illustrations show only one configuration of a retractor that is particularly useful in a cardiac tricuspid valve surgery. This embodiment is selected in order to set forth one of the best modes contemplated for the invention. The illustrated embodiment, however, is merely exemplary and should not be considered a limitation when interpreting the scope of the appended claims.

Figure 1:
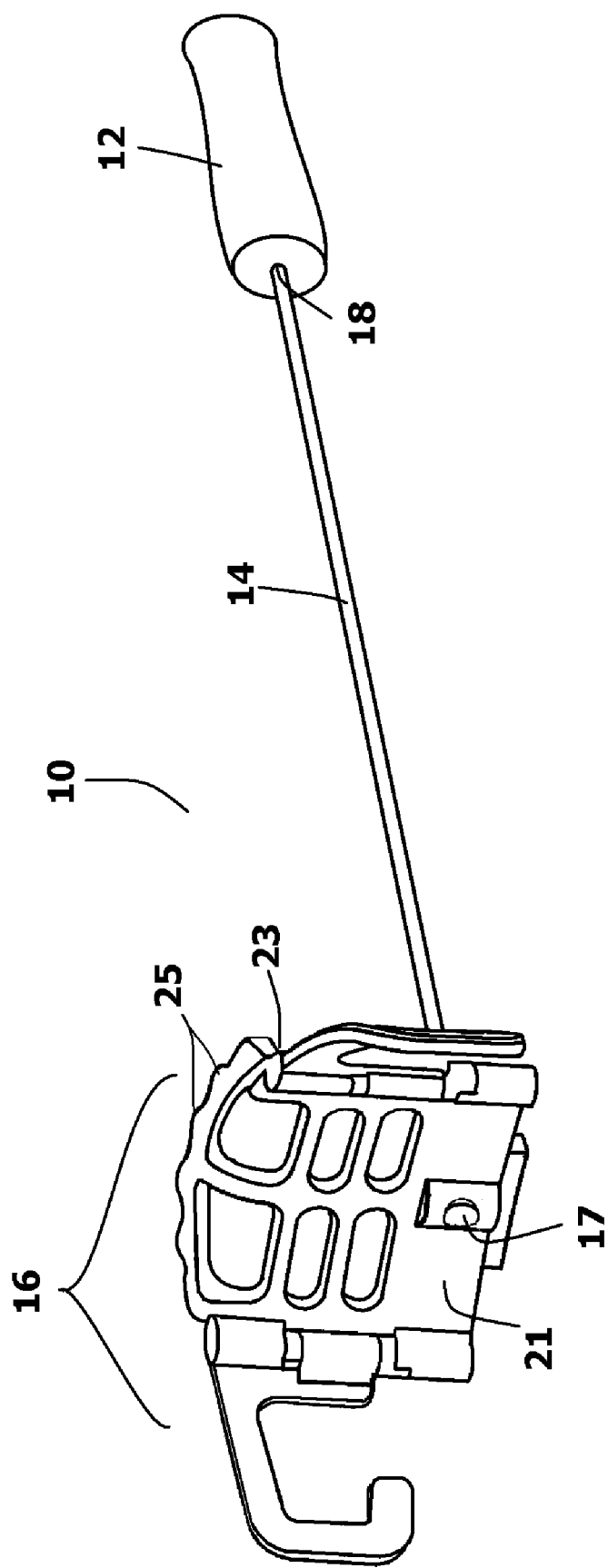
FIG. 1 is a perspective view of an exemplary embodiment of a retractor.

Referring to FIG. 1, a retractor 10 is shown. The retractor 10 has a handle 12, an elongated shaft 14, and a blade head assembly 16. The handle 12 is used by a surgeon to manipulate the blade head assembly 16 through an incision and into the body. The elongated shaft 14 has a first end 17 and an opposite second end 18. The first end 17 of the elongated shaft 14 engages the blade head assembly 16. The second end 18 of the elongated shaft 14 is coupled to the handle 12. The elongated shaft 14 is illustrated as being straight and unistructural. However, it will be understood that the elongated shaft 14 can contain bends and/or joints that enable the shape of the elongated shaft 14 to better meet the needs of a surgeon during a particular procedure.

Figure 2:
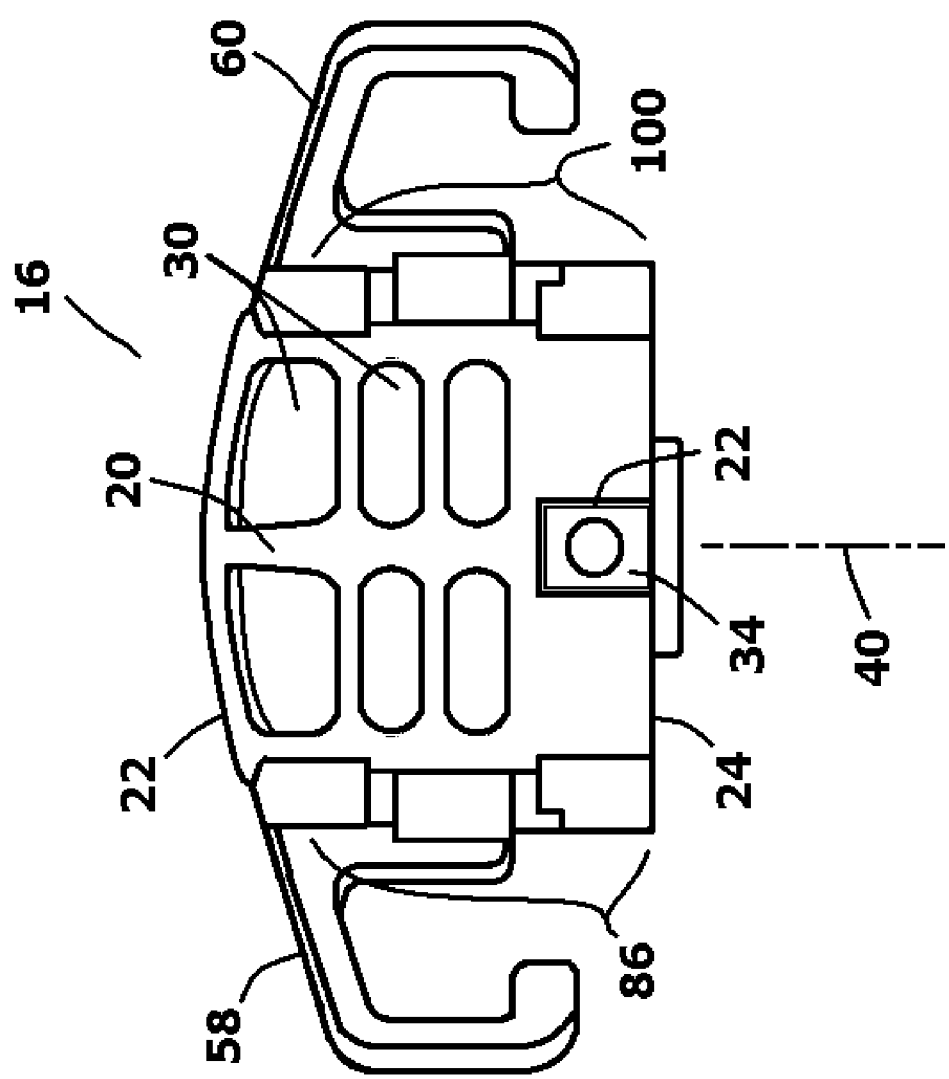
FIG. 2 is perspective view of the blade head assembly with rotatable arms in an open configuration.
Figure 3:
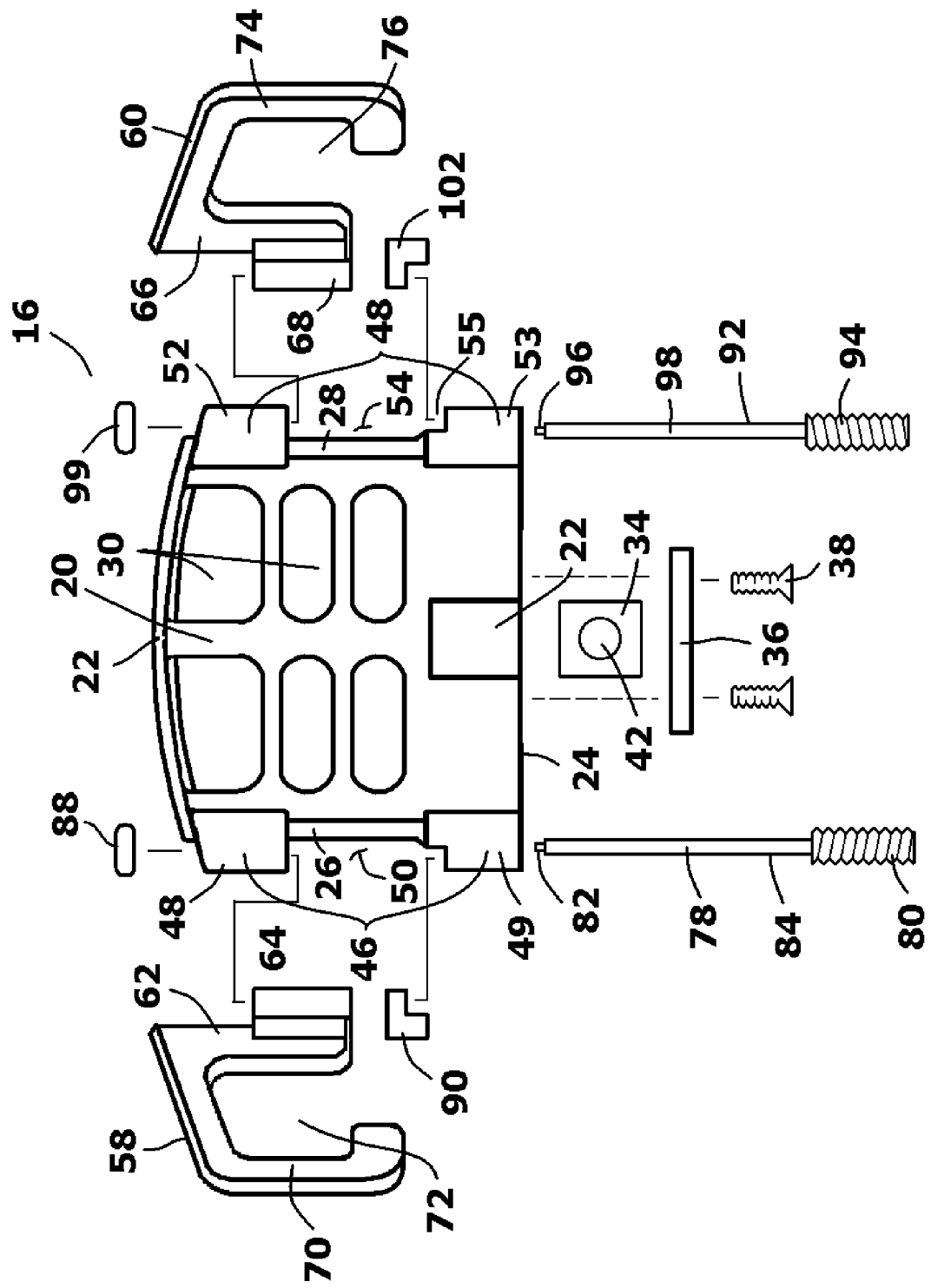
FIG. 3 is an exploded view of the blade head assembly shown in FIG. 2.

Referring to FIG. 2 and FIG. 3 in conjunction with FIG. 1, it can be seen that the blade head assembly 16 has a shaped central plate 20. The central plate 20 has a front surface 21 and a back surface 23 that are defined between a top edge 22, a bottom edge 24 and two side edges 26, 28. The central plate 20 is curved, wherein the front surface 21 is concave and the back surface 23 is convex. The central plate 20 also contains a plurality of openings 30 that extend through the central plate 20. The openings 30 enable blood, surgical rinse, and other liquids to flow through the central plate 20. The openings 30 also enable a surgeon to view tissue through the central plate 20. Lastly, the openings 30 reduce the weight and materials needed to manufacture the central plate 20 and the overall retractor 10.

A joint recess 32 is formed in the middle of the central plate 20 adjacent to the bottom edge 24. A hinge knuckle 34 is disposed in the joint recess 32. The hinge knuckle 34 is locked in place by a base plate 36 that attaches to the bottom edge 24 of the central plate 20 with mechanical fasteners 38. When locked in the joint recess 32, the hinge knuckle 34 is free to rotate about a rotational axis 40 that is parallel to the side edges 26, 28 of the central plate 20 and perpendicular to the bottom edge 24. A mounting hole 42 is formed through the hinge knuckle 34. The mounting hole 42 receives and engages the first end 17 of the elongated shaft 14. As such, it will be understood that when the elongated shaft 14 is engaged with the hinge knuckle 34, the hinge knuckle 34 can rotate about its rotational axis 40, and the orientation of the elongated shaft 14 relative the central plate 20 can be selectively adjusted throughout a range of movement.

The top edge 22 of the central plate 20 is bent toward the back surface 23 and terminates in a direction at or about ninety degrees from the rotational axis 40 of the hinge knuckle 34. In addition to being curved, the top edge 22 of the central plate 20 contains scalloped protrusions 25 along its length. The scalloped protrusions 25 and the complex curvature of the top edge 22 form a surgical rake that is effective of engaging tissue while the retractor 10 is in use.

Hinge barrel sets 44, 46 are formed on the side edges 26, 28 of the central plate 20. The first hinge barrel set 44 includes a first upper hinge barrel 48 and a first lower hinge barrel 49 that are spaced apart by a first gap 50. Likewise, the second hinge barrel set 46 includes a second upper hinge barrel 52 and a second lower hinge barrel 53 that are spaced apart by a second gap 54. Both the first lower hinge barrel 49 and the second lower hinge barrel 53 are internally threaded. Furthermore, both the first lower hinge barrel 49 and the second lower hinge barrel 53 contain limiting notches 55, 56, the purpose for which are later described.

A first rotatable arm 58 and a second rotatable arm 60 are provided. The first and second rotatable arms 58, 60 are mirrored in size and shape. The first rotatable arm 58 has base 62. A first knuckle cylinder 64 is affixed to the first rotatable arm 58. The first knuckle cylinder 64 is sized and shaped to fit into the first gap 50 between the first upper hinge barrel 48 and the first lower hinge barrel 49 on the first side edge 26 of the central plate 20. Likewise, the second rotatable arm 60 has base 66. A second knuckle cylinder 68 is affixed to the second rotatable arm 60. The second knuckle cylinder 68 is sized and shaped to fit into the second gap 54 between the second upper hinge 52 barrel and the second lower hinge barrel 53 on the second side edge 28 of the central plate 20.

A first hook-shaped extension 70 extends from the first base 62 to complete the first rotatable arm 58. The first hook-shaped extension 70 and the first base 62 define a first open central area 72. A second hook-shaped extension 74 extends from the second base 66 to complete the second rotatable arm 60. The second hook-shaped extension 74 and the second base 66 define a second open central area 76. The hook shape enables the first rotatable arm 58 and the second rotatable arm 60 to not only displace tissue within the body, but hook around elongated features, such as arteries.

A first hinge pin 78 is used to join the first rotatable arm 58 to the central plate 20. The first hinge pin 78 has a threaded head 80, a threaded foot 82 and a smooth shaft 84 between the threaded head 80 and the threaded foot 82. The threaded shaft 84 extends through the first lower hinge barrel 49, the first knuckle cylinder 64 and the first upper hinge barrel 48, therein forming a first hinge joint 86 between the first rotatable arm 58 and the central plate 20. The threaded head 80 of the first hinge pin 78 threads into the first lower hinge barrel 49. The threaded foot 82 of the first hinge pin 78 threads into a first end nut 88 beyond the first upper hinge barrel 48. A first hinge cam 90 is provided. The hinge cam 90 engages the limiting notch 55 in the first lower hinge barrel 49. This limits the rotational range of the first rotatable arm 58 about the first hinge joint 86.

A second hinge pin 92 is used to join the second rotatable arm 60 to the central plate 20. The second hinge pin 92 has a threaded head 94, a threaded foot 96 and a smooth shaft 98 between the threaded head 94 and the threaded foot 96. The shaft 98 extends through the second lower hinge barrel 53, the second knuckle cylinder 68 and the second upper hinge barrel 52, therein forming a second hinge joint 100 between the second rotatable arm 60 and the central plate 20. The second hinge joint 100 is parallel to the first hinge joint 86. The threaded head 94 of the second hinge pin 92 threads into the second lower hinge barrel 53. The threaded foot 96 of the second hinge pin 92 threads into a second end nut 99 beyond the second upper hinge barrel 52. A second hinge cam 102 is provided. The second hinge cam 102 engages the limiting notch 56 in the second lower hinge barrel 53. This limits the ability of the second rotatable arm 60 to rotate about the second hinge joint 100.

Figure 4:
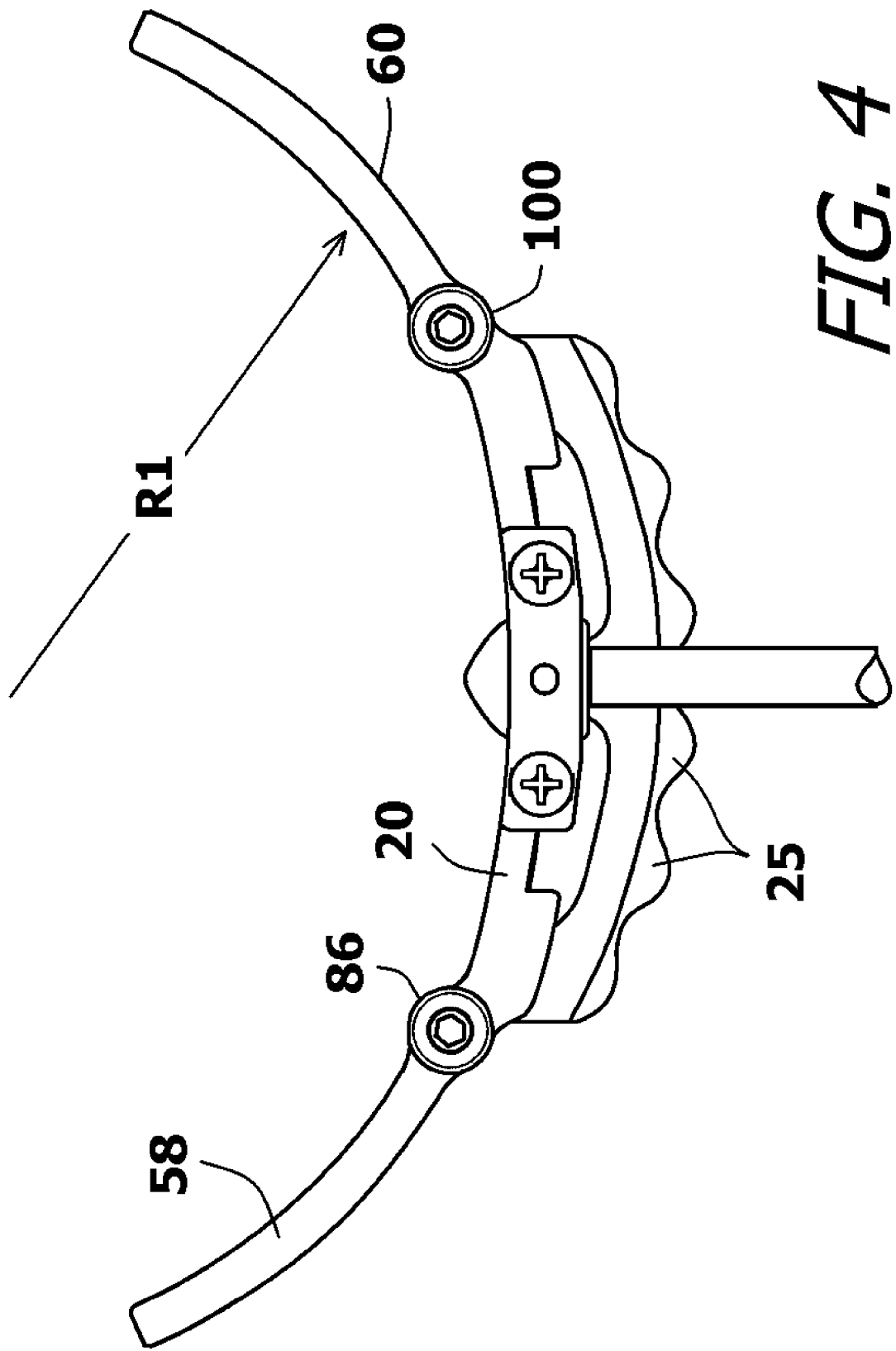
FIG. 4 is a bottom view of the blade head assembly shown in an open configuration.

Referring to FIG. 4 in conjunction with FIG. 3, it can be seen that the first rotatable arm 58 and the second rotatable arm 60 can be rotated about the first hinge joint 86 and the second hinge joint 100 respectively to fully open positions. In the fully open positions, it can be seen that the central plate 20, the first rotatable arm 58 and the second rotatable arm 60 are all curved and share a common radius of curvature R1. The radius of curvature R1 is equal to the width of the central plate 20 between the side edges 26, 28 of the central plate 20, plus or minus twenty percent.

Referring to FIG. 5 in conjunction with FIG. 3, it can be seen that the first rotatable arm 58 and the second rotatable arm 60 can be rotated about the first hinge joint 86 and the second hinge joint 100 respectively to fully folded positions. In the fully folded positions, the first rotatable arm 58 and the second rotatable arm 60 overlap. Furthermore, it should be noted that the first rotatable arm 58 and the second rotatable arm 60 do not contact the elongated shaft 14 as either the elongated shaft 14 or the rotatable arms 58, 60 move.

The first rotatable arm 58 and the second rotatable arm 60 can be selectively rotated about the first hinge joint 86 and the second hinge joint 100 to any positions between the fully open positions of FIG. 4 and the fully closed positions of FIG. 5. The positions of the first rotatable arm 58 and the second rotatable arm 60 are set by the surgeon. The surgeon selects a configuration that he/she requires. The first hinge joint 86 and the second hinge joint 100 are both adjustable friction joints. That is, the force needed to rotate the first rotatable arm 58 about the first hinge joint 86 and to rotate the second rotatable arm 60 about the second hinge joint 100 can be selectively adjusted. The force needed to rotate the first rotatable arm 58 and/or the second rotatable arm 60 is adjusted by tightening and/or loosening the hinge pins 78, 92. Likewise, by firmly tightening the hinge pins 78, 92, the position of the first rotatable arm 58 and the position of the second rotatable arm 60 can be locked in place. As has been previously explained, the first hinge pin 78 has a threaded head 80 that engages the first lower hinge barrel 49. By selectively tightening or loosening the first hinge pin 78, the tension within the first hinge joint 86 can be altered. As tension forces increase, friction increases as does the force needed to alter the first hinge joint 86. Likewise, the second hinge pin 92 has a threaded head 94 that engages the second lower hinge barrel 53. By selectively tightening and loosening the second hinge pin 92, the tension within the second hinge joint 100 can be altered. As tension forces increase, friction increases as does the force needed to alter the second hinge joint 100.

Returning to FIG. 1, it will be understood that to use the present invention retractor 10, a first incision is made in a body cavity. The blade head assembly 16 is then inserted into the body cavity through that the incision using any appropriately sized set of forceps. The blade head assembly 16 has a narrow cross section. As such, only a narrow incision needs to be made and the blade head assembly 16 can be advanced through the incision with minimal disruption to surrounding tissue.

Once the blade head assembly 16 is in place, another small incision is made into the body cavity. The elongated shaft 14 is then advanced through the second incision. Once in the body cavity, the elongated shaft 14 is connected to the blade head assembly 16. Once the blade head assembly 16 is in place, the orientation of the central plate 20 and the two rotatable arms 58, 60 can then be altered to the needs of the surgeon.

It will be understood that the embodiment of the present invention that is illustrated and described is merely exemplary and that a person skilled in the art can make many variations to that embodiment. All such embodiments are intended to be included within the scope of the present invention as defined by the appended claims.

What is claimed is:

1. A retractor assembly, comprising:
   a central plate having a top edge, a bottom edge, a first side edge and a second side edge;
   a joint recess extending into said central plate from said bottom edge;
   a base plate that attaches to said bottom edge of said central plate spanning said joint recess along said bottom edge;
   a hinge knuckle disposed in the joint recess, said hinge knuckle being retained in said joint recess by said base plate, wherein said hinge knuckle is free to rotate in said joint recess about a rotational axis that is parallel to said first side edge of said central plate, parallel to said second side edge of said central plate, and perpendicular to said bottom edge of said central plate;
   a first rotatable arm attached to said first side edge of said central plate with a first hinge joint, wherein said first rotatable arm can be rotated about said first hinge joint through a first range of motion relative to said central plate;
   a handle; and
   an elongated shaft that extends from said handle to said hinge knuckle, wherein said elongated shaft connects to said hinge knuckle.

2. The assembly according to claim 1, further including a second rotatable arm attached to said second side edge of said central plate with a second hinge joint, wherein said second rotatable arm can be rotated about said second hinge joint through a second range of motion relative to said central plate.

3. The assembly according to claim 2, wherein said first rotatable arm and said second rotatable arm are mirrored in size and shape.

4. The assembly according to claim 2, wherein said first hinge joint and said second hinge joint are parallel joints.

5. The assembly according to claim 2, wherein said first rotatable arm is curved, said second rotatable arm is curved, and said central plate is curved between said first side edge and said second side edge, wherein said first rotatable arm, said second rotatable arm and said central plate share a common radius of curvature.

6. The assembly according to claim 1, wherein said first rotatable arm is curved and said central plate is curved between said first side edge and said second side edge, wherein said first rotatable arm and said central plate have a common radius of curvature.

7. The assembly according to claim 1, wherein said top edge contains a plurality of scalloped protrusions.

8. The assembly according to claim 1, wherein said first hinge joint is a friction hinge that requires a threshold force to move, wherein said first rotatable arm attaches to said first side edge of said central plate with a threaded pin that can be selectively tightened and loosened to alter said threshold force.

9. A retractor assembly, comprising:
   a central plate having a top edge, a bottom edge, a first side edge and a second side edge;
   a joint recess extending into said central plate from said bottom edge;
   a hinge knuckle disposed in said joint recess, said hinge knuckle having a mounting hole formed therein, wherein said hinge knuckle is free to rotate in said joint recess about a rotational axis that is parallel to said first side edge of said central plate, parallel to said second side edge of said central plate, and perpendicular to said bottom edge of said central plate;
   a first rotatable arm attached to said first side edge of said central plate with a first hinge joint, wherein said first rotatable arm can be rotated about said first hinge joint through a first range of motion relative to said central plate;
   a second rotatable arm attached to said second side edge of said central plate with a second hinge joint, wherein said second rotatable arm can be rotated about said second hinge joint through a second range of motion relative to said central plate; and
   an elongated shaft that connects to said mounting hole of said hinge knuckle.

10. The assembly according to claim 9, wherein said joint recess is midway between said first side edge and said second side edge.

11. The assembly according to claim 9, wherein said first rotatable arm and said second rotatable arm are mirrored in size and shape.

12. The assembly according to claim 9, wherein said first hinge joint and said second hinge joint are parallel joints.

13. The assembly according to claim 9, wherein said first rotatable arm is curved, said second rotatable arm is curved, and said central plate is curved between said first side edge and said second side edge, wherein said first rotatable arm, said second rotatable arm and said central plate share a common radius of curvature.

14. The assembly according to claim 9, wherein said first hinge joint is a friction hinge that requires a threshold force to move, wherein said first rotatable arm attaches to said first side edge of said central plate with a threaded pin that can be selectively tightened and loosened to alter said threshold force.

15. The assembly according to claim 9, wherein said central plate has a concave front surface and a convex back surface that extend between said first side edge and said second side edge.

16. The assembly according to claim 15, wherein multiple openings are formed through said central plate between said concave front surface and said convex back surface.

17. The assembly according to claim 15, wherein said central plate has a top edge that extends between said first side edge and said second side edge, wherein said top edge is bent toward said convex back surface.

18. The assembly according to claim 9, wherein said first rotatable arm and said second rotatable arm are both hook shaped and define central openings.

19. The assembly according to claim 9, wherein said elongated shaft is selectively attachable to and detachable from said mounting hole of said hinge knuckle.

* * * * *